(12) United States Patent
Martinelli

(10) Patent No.: US 7,104,985 B2
(45) Date of Patent: Sep. 12, 2006

(54) APPARATUS AND METHOD FOR CAUSING SELECTIVE NECROSIS OF ABNORMAL CELLS

(76) Inventor: Michael A. Martinelli, 58 Wedgemere Ave., Winchester, MA (US) 01890

( * ) Notice: Subject to any disclaimer, the term of this patent is extended or adjusted under 35 U.S.C. 154(b) by 61 days.

(21) Appl. No.: 10/760,959

(22) Filed: Jan. 20, 2004

(65) Prior Publication Data

US 2004/0176826 A1    Sep. 9, 2004

Related U.S. Application Data

(60) Provisional application No. 60/452,466, filed on Mar. 6, 2003.

(51) Int. Cl.
*A61B 18/04* (2006.01)
(52) U.S. Cl. .................... 606/31; 128/898; 606/33
(58) Field of Classification Search ................. 128/898; 606/27–34; 607/96
See application file for complete search history.

(56) References Cited

U.S. PATENT DOCUMENTS

| | | | |
|---|---|---|---|
| 4,190,053 A * | 2/1980 | Sterzer | 607/96 |
| 4,931,047 A * | 6/1990 | Broadwin et al. | 604/22 |
| 5,211,625 A * | 5/1993 | Sakurai et al. | 604/22 |
| 5,330,517 A * | 7/1994 | Mordon et al. | 607/89 |
| 5,573,533 A * | 11/1996 | Strul | 606/34 |
| 5,769,847 A * | 6/1998 | Panescu et al. | 606/42 |
| 5,776,092 A * | 7/1998 | Farin et al. | 604/22 |
| 5,891,134 A * | 4/1999 | Goble et al. | 606/27 |
| 6,022,346 A * | 2/2000 | Panescu et al. | 606/27 |
| 6,053,909 A * | 4/2000 | Shadduck | 606/3 |
| 6,165,172 A * | 12/2000 | Farley et al. | 606/33 |
| 6,203,540 B1 * | 3/2001 | Weber | 606/15 |
| 6,231,594 B1 * | 5/2001 | Dae | 607/96 |
| 6,251,110 B1 * | 6/2001 | Wampler | 606/49 |
| 6,293,943 B1 * | 9/2001 | Panescu et al. | 606/41 |
| 6,451,044 B1 * | 9/2002 | Naghavi et al. | 607/96 |
| 6,506,189 B1 * | 1/2003 | Rittman et al. | 606/41 |
| 6,520,185 B1 * | 2/2003 | Bommannan et al. | 128/898 |
| 6,593,130 B1 * | 7/2003 | Sen et al. | 435/285.2 |
| 2002/0156470 A1 * | 10/2002 | Shadduck | 606/41 |

* cited by examiner

*Primary Examiner*—Henry M Johnson, III
(74) *Attorney, Agent, or Firm*—Donald E. Mahoney

(57) ABSTRACT

A method and apparatus adapted to utilize means for controlling a plurality of energy pulses to repetitively increase and decrease the temperature of a target tissue with a prescribed timing for each temperature change and specific peak temperature for each temperature change to provide selected necrosis of diseased cells.

1 Claim, 12 Drawing Sheets

APPARATUS AND METHOD FOR CAUSING SELECTIVE NECROSIS OF ABNORMAL CELLS

CROSS-REFERENCE TO RELATED APPLICATIONS

This application claims the benefit of U.S. provisional application No. 60/452,466, filed Mar. 6, 2003

FEDERALLY SPONSORED RESEARCH

Not Applicable

BACKGROUND OF THE INVENTION

1. Field of the Invention

The present invention relates to an apparatus and method using a modified new form of hyperthermia for treating cancerous tumors and multi-site or diffuse cancers.

2. Description of Related Art

As is known in the art, the use of hyperthermia to treat tumors can be effective in causing necrosis of cancer cells by a process called coagulative necrosis. However this process exhibits very little selectivity since cancerous cells are only slightly more vulnerable than normal cells to hyperthermia. As a result, a conventional hyperthermia process is impractical where there are both normal and abnormal cells present.

It has been the object of known methods and apparatus using conventional sources of applied energy such as microwave energy, radio frequency energy (RF heating), magnetic heating, interstitial laser fiber heating and ultrasonic energy to precisely match the focus of the applied energy within the cancerous tumor. Such tumors are spatially confined and can be so targeted. This is considered very important in an attempt to minimize the destruction of nearby normal cells. A disadvantage of such methods and apparatus is that they will be ineffective in treating cancer cells which may have spread throughout an organ or into neighboring lymph nodes. In addition, such directed heat methods are of no use in treating diffuse or multi-site cancers in which the cancer cells are intermingled with normal cells that should not be destroyed or removed.

SUMMARY OF THE INVENTION

According to the present invention, an apparatus and method for treating a target tissue sensitive to changes in target tissue temperature comprising means for directing a plurality of energy pulses toward the target tissue, and means for controlling the plurality of energy pulses to assist in pulsating the temperature of the target tissue over a predetermined period of time.

BRIEF DESCRIPTION OF THE DRAWINGS

The invention is better understood by reading the following detailed description with reference to the accompanying figures in which like reference numerals refer to like elements throughout and which.

DETAILED DESCRIPTION OF THE PREFERRED EMBODIMENT

Figure 1A:
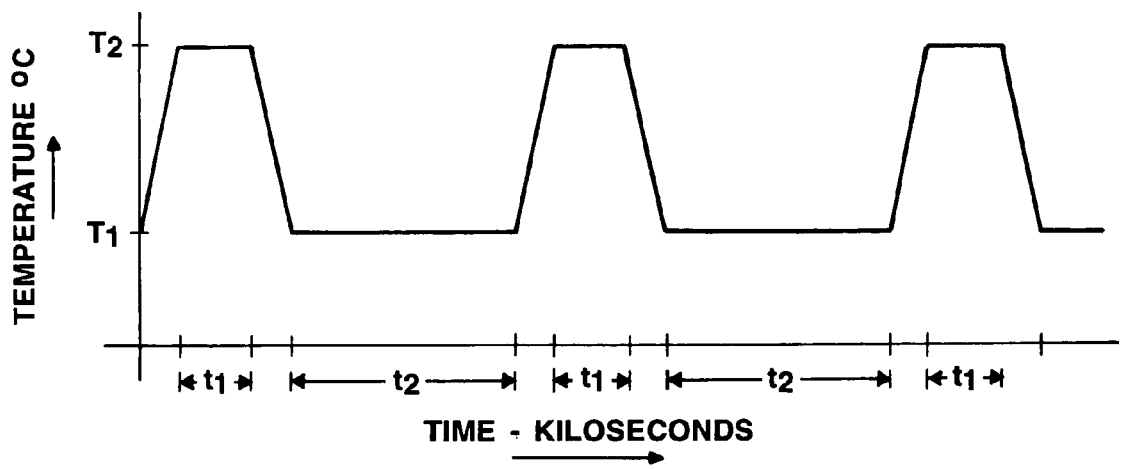
FIG. 1A shows a graph of periodic pulses of uniform peak temperature representing Temperature vs. Time profile of a target tissue subjected to a plurality of positive and negative energy pulses.

The apparatus shown in the drawings is arranged to direct a plurality of positive and negative energy pulses toward a target tissue for alternately causing the heating and cooling of diseased tissue. The provision of a negative energy pulse for cooling of target tissue is in part achieved through blood flow and may be supplemented by a cooling device described below. The apparatus is intended to assist in pulsating the temperature of the target tissue over a predetermined period of time. The apparatus assists in providing a systematic increase and decrease of temperature in the target tissue. The increase and decrease of target tissue temperature may be graphically represented as periodic pulses of uniform, peak temperature, or periodic pulses of non-uniform peak temperature, or a periodic pulses of non-uniform peak temperature, or a periodic pulses of uniform peak temperature. As used herein, the term target tissue will refer to diseased and normal cells that are intermingled or nearby, all of which will be subject to treatment. In some applications, the apparatus may be operated to cause the temperature of the target tissue cells to pulsate in time in a periodic or a periodic manner.

The apparatus comprises means for controlling the plurality of energy pulses to repetitively increase and decrease the temperature of the target tissue (hereinafter "excursions") with a prescribed timing for each excursion and specific peak temperatures for each excursion. The specific peak temperature of the target tissue for each excursion may be the same (uniform) or different (non-uniform). The repetition rate and excursion temperatures of the target tissue are selected to cause selective necrosis of cells containing one or more defective proteins. As used herein, the term defective protein means a protein containing an error within its structure. Cancer cells typically contain a set of between 3 and 7 of such defective protein types. This set of defective proteins is the same in all cells of a given cancer, since the entire cancer derives from one initial cell.

Referring to FIG. 1A, there is shown a graph of periodic pulses of uniform peak temperature representing a Temperature (° C.) vs. Time (kilo-seconds) profile of a target tissue subjected to a plurality of positive and negative energy pulses from apparatus described below. The energy pulses assist in periodically increasing the temperature of the target tissue from a temperature $T_1$, to a temperature $T_2$, for a first period, $t_1$, and then decreasing the temperature of the target tissue from temperature $T_2$ back to temperature $T_1$ for a second period $t_2$. This process, periodically increasing and decreasing the temperature of a target tissue, is repeated for a predetermined period or until the cells containing the targeted defective protein will either die immediately (coagulative necrosis) or within 24 hours (delayed necrosis). Cells not containing the targeted defective protein but only error-free versions of this protein (healthy cells) will survive this treatment. This process of periodically increasing and decreasing the temperature of a target tissue for uniform time periods is referred to as synchronized hypothermia.

Figure 1B:
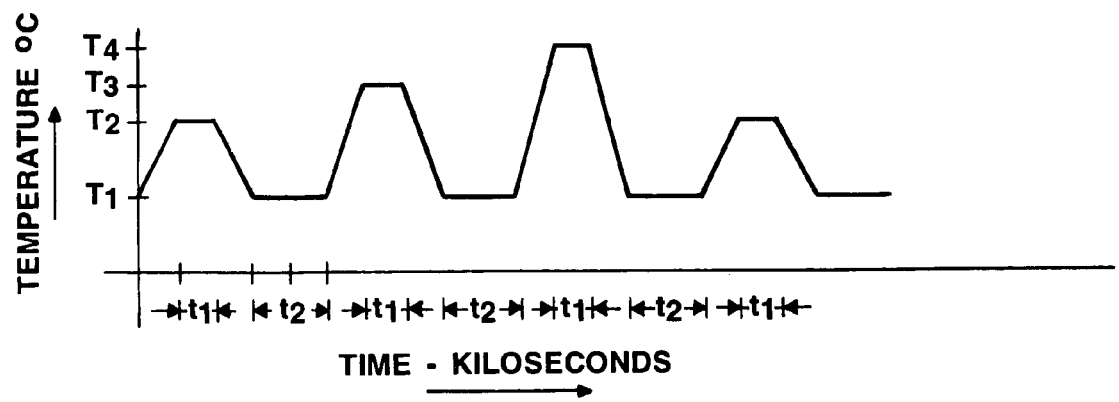
FIG. 1B shows a graph of periodic pulses of non-uniform peak temperature representing Temperature vs. Time profile of a target tissue subject to a plurality of positive and negative energy pulses.

Referring to FIG. 1B, there is shown a graph of periodic pulses of non-uniform peak temperature representing a Temperature (° C.) vs. Time (kilo-seconds) profile of a target tissue subjected to a plurality of positive and negative energy pulses from apparatus described below. The energy pulses assist in periodically increasing the temperature of the target tissue from a temperature $T_1$, to a temperature $T_2$ for a first period, $t_1$ and then decrease the temperature of the target tissue from $T_2$ back to temperature $T_1$ for a second period of time $t_2$. The positive and negative energy pulses are selected to assist in the provision of a non-uniform change in the peak temperature, $T_2$, or temperature excursions of the target tissue and substantially uniform pulse spacing of period $t_2$ between such pulses.

Figure 1C:
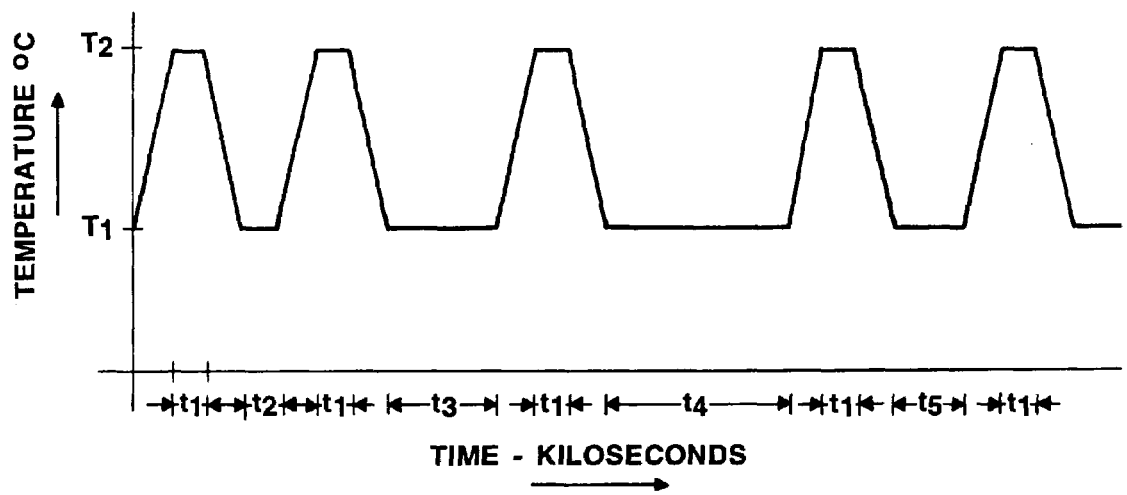
FIG. 1C shows a graph of a periodic pulses of uniform peak temperature representing Temperature vs. Time profile of a target tissue subjected to a plurality of positive and negative energy pulses.

Referring to FIG. 1C, there is shown a graph of a periodic pulses of substantially uniform peak temperature representing Temperature (° C.) vs. Time (kilo-seconds) profile of a target tissue subjected to a plurality of positive and negative energy pulses from apparatus described below. The energy pulses assist in a periodically increasing the temperature of the target tissue from a temperature $T_1$ to a temperature $T_2$ for a first time period, $t_1$, and then decreasing the temperature of the target tissue from $T_2$ back to temperature $T_1$, for a second period of time $t_2$. The positive and negative energy pulses are selected to assist in the provision of substantially uniform change in the peak temperature, $T_2$, or temperature excursions of the target tissue and non-uniform pulse spacing of periods $t_2, t_3, t_4, t_5$, between such pulses. It is believed that the use of positive and negative energy pulses to provide a Temperature (° C.) vs. Time (kilo-seconds) profile of a target tissue as shown in FIG. 1C may be useful in treating certain types of cancer.

Figure 1D:
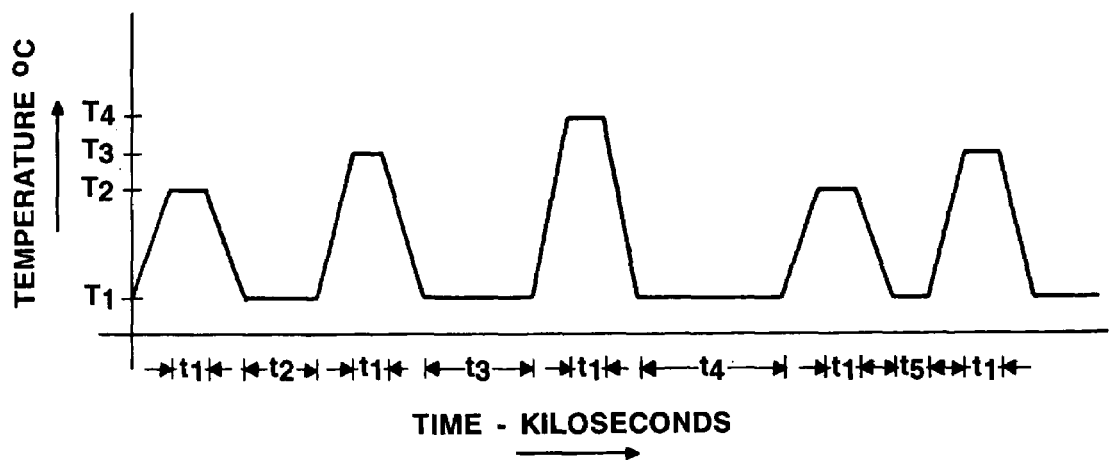
FIG. 1D shows a graph of a periodic pulses of non-uniform peak temperature representing Temperature vs. Time profile of a target tissue subject to a plurality of positive and negative energy pulses.

Referring to FIG. 1D, there is shown a graph of a periodic pulses of non-uniform height representing a Temperature (° C.) vs. Time (kilo-seconds) profile of a target tissue subjected to a plurality of positive and negative energy pulses from apparatus described below. The energy pulses assist in a periodically increasing the temperature of the target tissue from a temperature $T_1$ to a temperature $T_2$ for a first time period, $t_1$, and then decreasing the temperature of the target tissue from $T_2$ back to temperature $T_1$ for a second period of time $t_2$. The positive and negative energy pulses are selected to assist in the provision of a substantially non-uniform change in the peak temperature $T_2, T_3, T_4$, or temperature excursions of the target tissue and non-uniform pulse spacing or periods $t_2\ t_3\ t_4, t_5$ between such peak pulses. This process of treatment is referred to as synchronized chirp hypothermia. It is believed that the use of synchronized chirp hypothermia may significantly decrease the treatment time in certain types of cancer.

It should be understood that in practice specific cancer cells may require more intricate energy pulses that may be determined by experiments performed on such cancer cells. Such energy pulses might result in a treatment that could be described as synchronized hyperthermia or synchronized chirp hyperthermia or such energy pulses may cause a completely separate optimized Temperature (° C.) vs. Time (kilo-seconds) profile (hereinafter "OTTP") in the target tissue. In addition to an OTTP, there are other slightly different Temperature (° C.) vs. Time (kilo-seconds) profiles that may also selectively necrose cancer cells and not damage normal cells. The OTTP and the various other slightly different Temperature (° C.) and Time (kilo-seconds) profiles are hereinafter referred to as effective Temperature (° C.) vs. Time (kilo-seconds) profiles ("ETTP").

Figure 2:
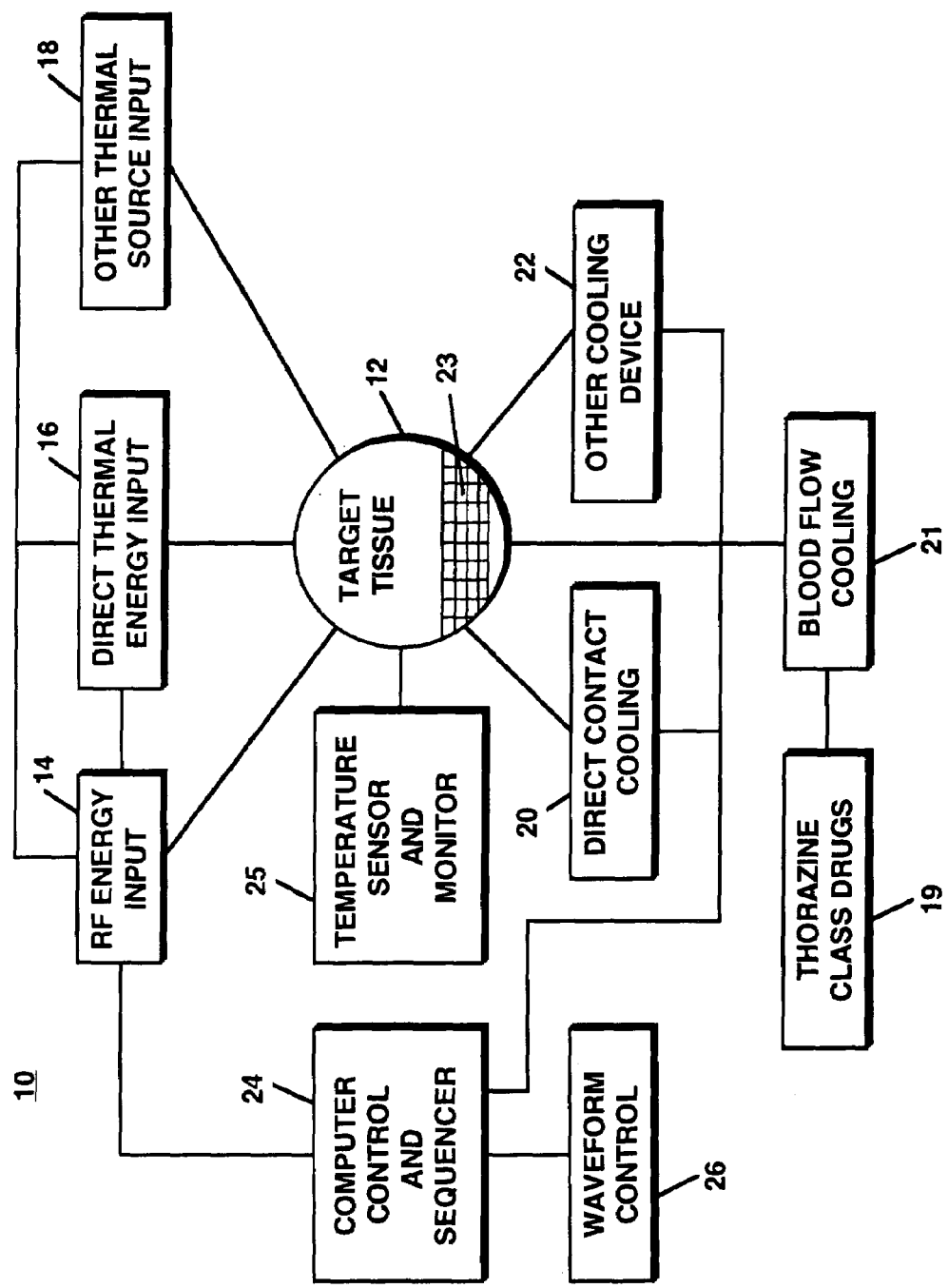
FIG. 2 shows a block diagram of apparatus arranged to provide a plurality of energy pulses to the target tissue.

Referring to FIG. 2, there is shown a block diagram of apparatus 10 arranged to provide a plurality of energy pulses to the target tissue. For ease of analysis, the target tissue is divided into a collection of pixels. The size of each tissue pixel 23 in the target tissue 12 is such that all cells within a tissue pixel 23 are subjected to substantially the same Time vs. Temperature profile in response to the energy pulses provided by apparatus 10. Those pixels 23 experiencing the OTTP will have their cancer necrose a bit sooner in the treatment sequence than will the tissue pixels 23 that experience a slightly different Temperature (° C.) vs. Time (kilo-seconds). However, all pixels 23 will be effectively treated by operation of apparatus 10 (or will receive an ETTP treatment). Many of the normal cells in an organ may have protein errors, but such errors are insufficient in number to turn the cells cancerous. As time proceeds, new protein errors will occur in the daughter cells of the normal cells that already have protein errors. It is by this route of increasing protein errors that most cancers occur. An ETTP is usually selected to target one specific protein error present in the cancerous cells. The ETTP will also necrose normal cells that happen to have that specific protein error. Thus, it is possible to subject a target tissue to an ETTP treatment when no cancer is present in order to remove pre-cancerous cells as a prophylactic measure, making it more difficult for a cancer to start. This will cleanse the organ of poorly functioning cells (cells with protein errors that are not sufficient to initiate a cancer but are sufficient to diminish the performance of the cell) and thus improving the function of the organ. The operation of apparatus 10 on an entire organ or a target tissue 12 comprising a plurality of individual tissue pixels 23 involves a finite difference analysis to assure that each tissue pixel 23 is subjected to an effective Time vs. Temperature profile for the given cancer. The energy pulses may be generated by one or more sources operating separately or in combination. For example, a prior art R.F. (Radio Frequency) generator 14 may be arranged to direct a series of R.F. energy pulses or R.F. energy input toward the target tissue 12. The R.F. energy pulses are intended to increase the temperature of the target tissue 12. Another source of energy pulses may be a prior art heat source 16 in direct thermal contact with the target tissue. Other energy sources 18 such as prior art ultrasonic energy sources may also be used to direct energy pulses toward the target tissue 12.

Cooling of the target tissue 12 may be arranged by use of prior art cooling devices 20 in direct contact with the target tissue 12. In addition, other prior art cooling devices 22 not in direct contact with the target tissue 12 may be used to control temperature. An example of target tissue cooling may involve the use of a pair of displaced hypodermic needles inserted into the target tissue so that when a cooling fluid is pumped through one needle such fluid may be extracted by the other needle.

Blood flow cooling may be used to control temperature of target tissue 12. The degree of blood flow cooling can be moderated through the use of Thorazine Class drugs 19.

The operation of the various sources of energy pulses or energy input 14, 16 and 18 and the various sources of heat extraction or cooling devices 20, 21, 22 are controlled by a computer-driven sequencer 24. A waveform control device 26 is coupled to a sequencer 24 and arranged to provide a desired waveform for the energy pulses so that each tissue pixel 23 within the target tissue 11 is experiencing a Temperature vs. Time profile that is effective for causing necrosis of the cancer cells while sparing the normal cells. A prior art temperature sensor and monitor 25 is coupled to the target tissue 12 and the computer control and sequencer 24 so as to provide an indication of the actual temperature of the target tissue 12 to the computer control and sequencer 24 to achieve the desired Temperature vs. Time profile.

Figure 3:
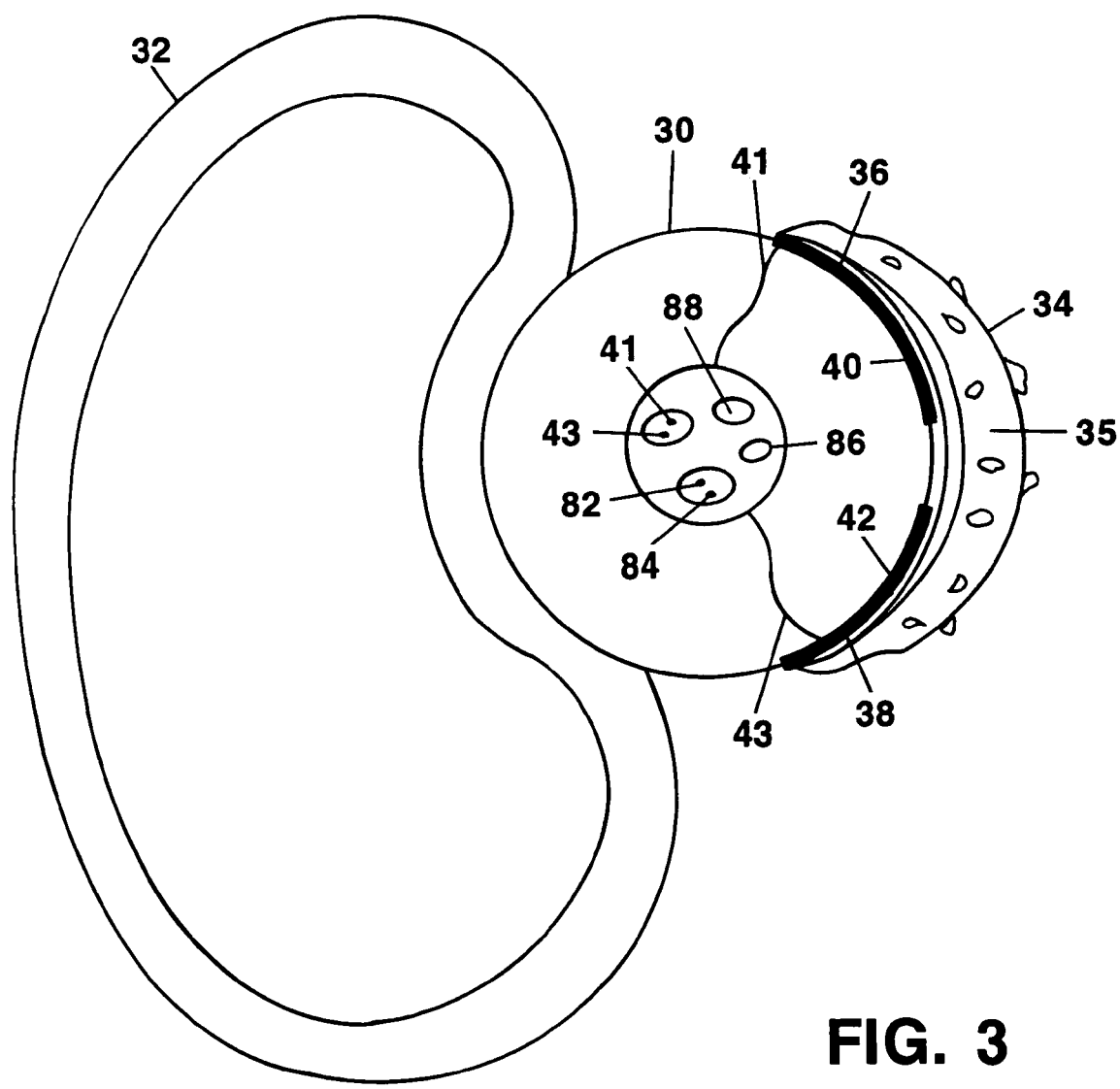
FIG. 3 shows a cross-sectional end view of a tubular device suitable for treating pancreatic cancer.
Figure 4:
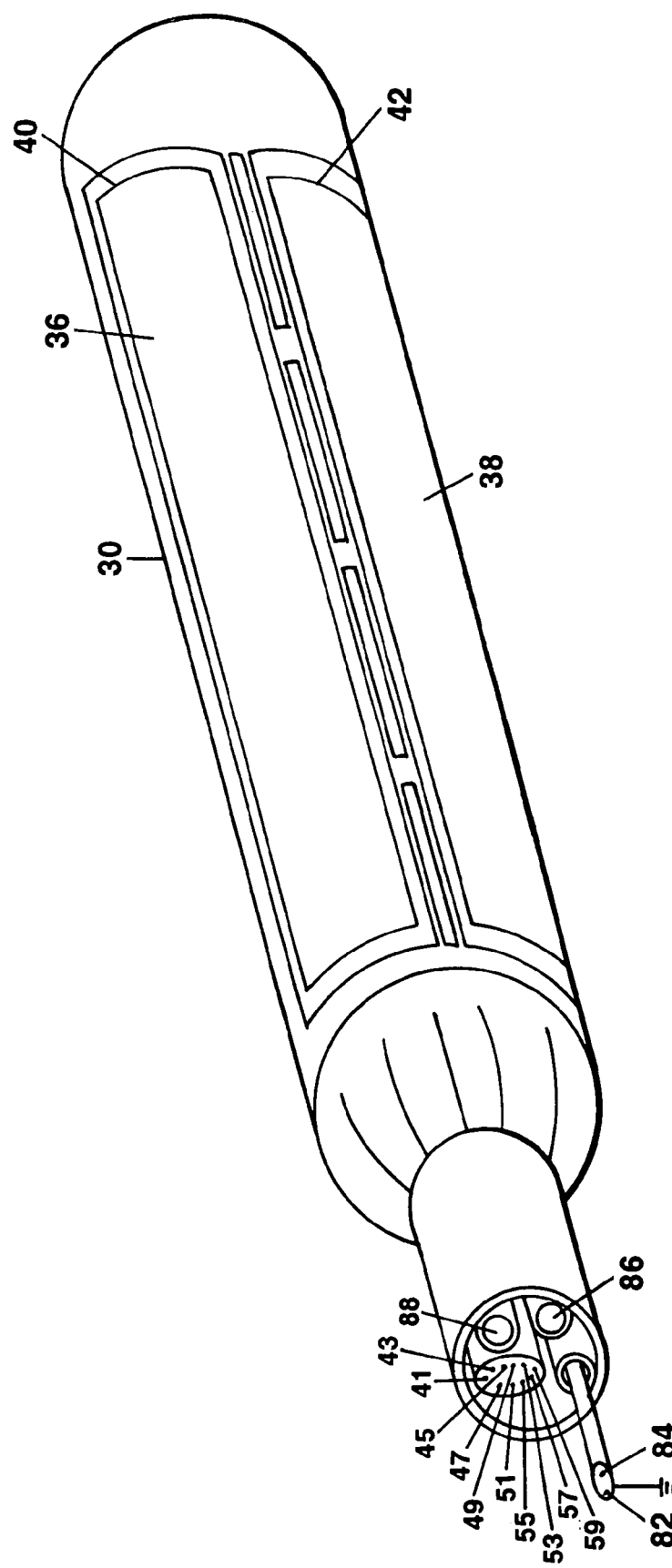
FIG. 4 shows a perspective view of the device shown in FIG. 3.

Referring to FIG. 3 and FIG. 4, there is shown a cross-sectional end view and a perspective view, respectively, of a device 30 suitable for treating pancreatic cancer when used in combination with the apparatus 10 shown in FIG. 2. The device 30 is in the form of a cylindrical inflatable balloon that is positioned between the stomach 32 and the pancreas 34, causing the pancreas 34 to be flattened and draped on the surface of device 30 adjacent to outside protective surfaces 36, 38, of device electrodes 40, 42. The protective surfaces 36, 38 allow for R.F. current flow from the electrodes 40, 42 into the pancreas 36 while protecting the metal film on electrodes 40, 42 from electrolytic damage. The device electrodes to 42 are connected by wires 41, 43 to R.F. generator 14 shown in FIG. 2. In addition, tubular members 86, 88 are disposed within device 30 to allow inflation of device 30 when a fluid at a desired temperature is pumped through tubular members 86, 88. Device 30 is arranged to provide heating and cooling of the tissue of pancreas 34 in thermal contact with temperature-controlled fluid pumped through tubular members 86, 88.

Figure 5:
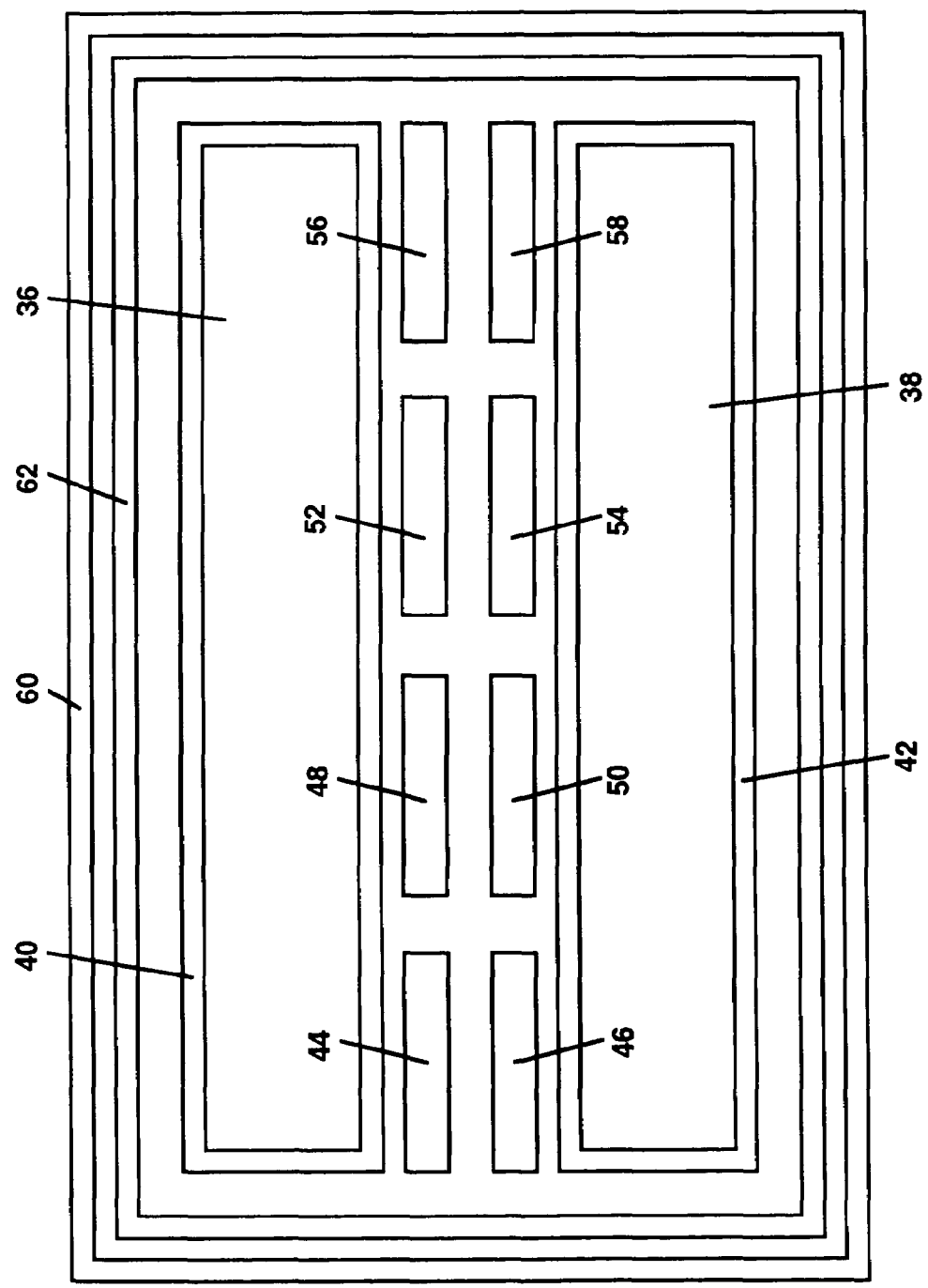
FIG. 5 shows a top view of electrodes on a surface of the device shown in FIG. 4.

Referring to FIG. 5, there is shown a top view of device electrodes 40, 42 as well as a series of smaller electrode rings 60, 62 which may be added to surround device electrodes 40, 42. The electrode rings 60, 62 are arranged to minimize edge concentration of R.F. current flowing to device electrodes 40, 42 when device 30 is subjected to energy from R.F. generator 14. The electrode rings 60, 62 allow a more even distribution of R.F. current flowing to device electrodes 40, 42. A series of electrode pairs 44 and 46, 48 and 50, 52 and 54, 56 and 58 are positioned on the surface of device 30 between electrodes 40, 42. The electrical resistance between electrode pair 44 and 46 serve to provide an electrical signal that is calibrated to indicate the approximate temperature within pancreas 34. Other electrode pairs 48 and 50, 52 and 54, 56 and 58 perform the same function at different locations along the length of device 30. Referring back to FIG. 4, wires 45, 47, 49, 51, 53, 55, 57, 59 connect electrode pairs 44 and 46, 48 and 50, 52 and 54, 56 and 58 to temperature sensor and monitor 25 in FIG. 2.

Figure 6:
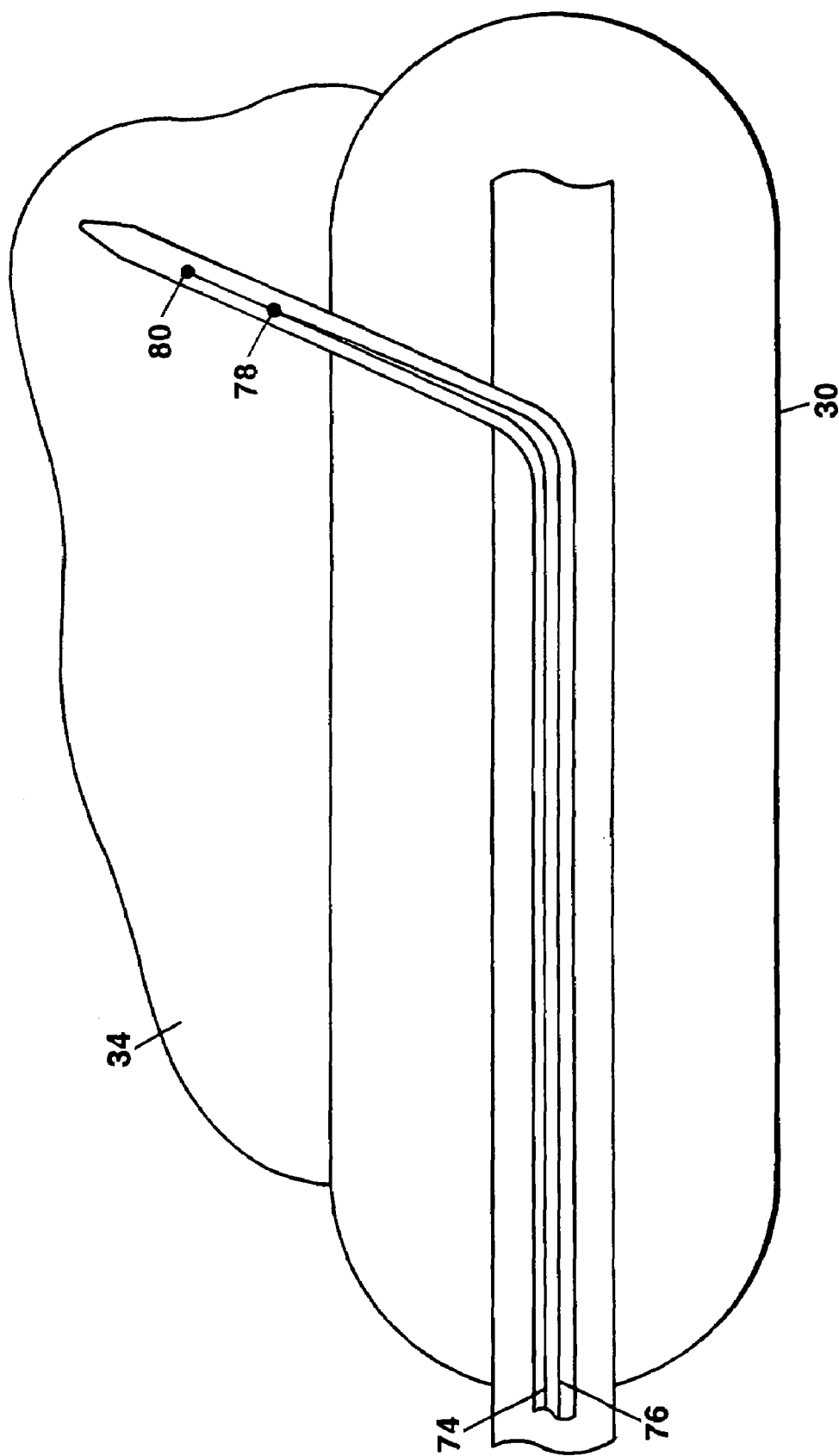
FIG. 6 is a cross-sectional side view of the device shown in FIG. 4.

Referring to FIG. 6, there is shown a cross-sectional side view of device 30 with temperature sensors 74, 76 each having an end 78, 80 which may be moved in and out of device 30 and into pancreas 34 to sense temperature at various internal points in pancreas 34 during treatment. Temperature sensors 74, 76 may be used to calibrate actual temperature within pancreas 34 with measured electrical resistance between electrode pairs 44 and 46, 48 and 50, 52 and 54, 56 and 58. Referring back to FIG. 4, the other ends 82, 84 of sensors 74, 76 are connected to the temperature sensor and monitor 25 shown in FIG. 2.

Figure 7:
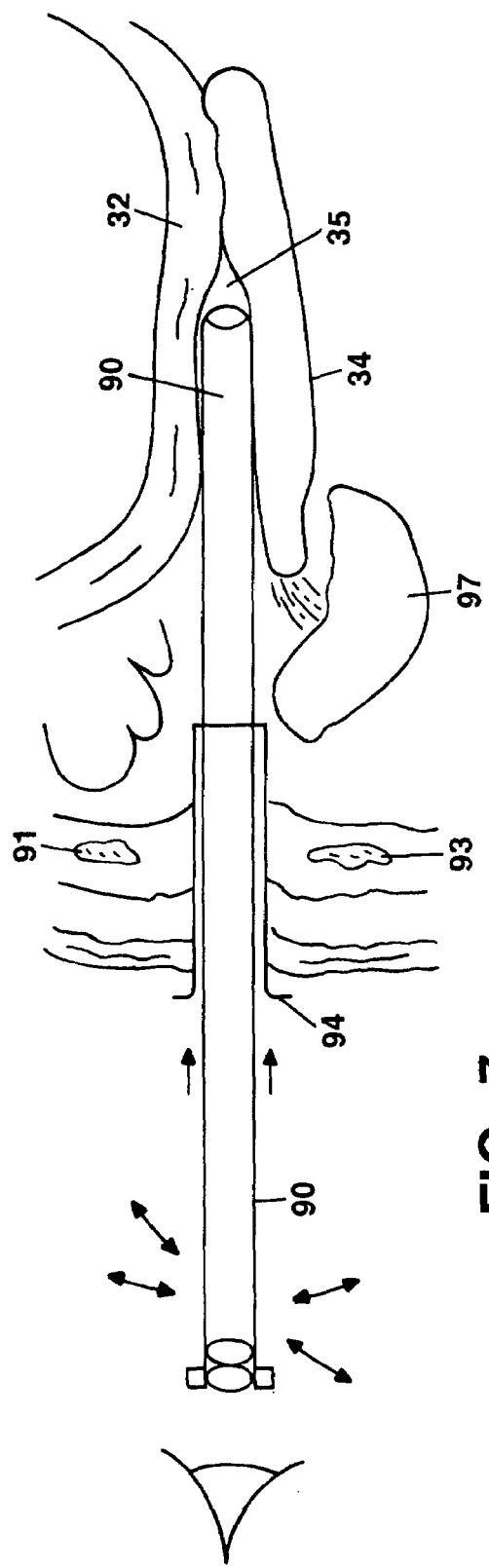
FIG. 7 and FIG. 8 together illustrate a method of inserting the device shown in FIG. 3 into the body of a patient.
Figure 8:
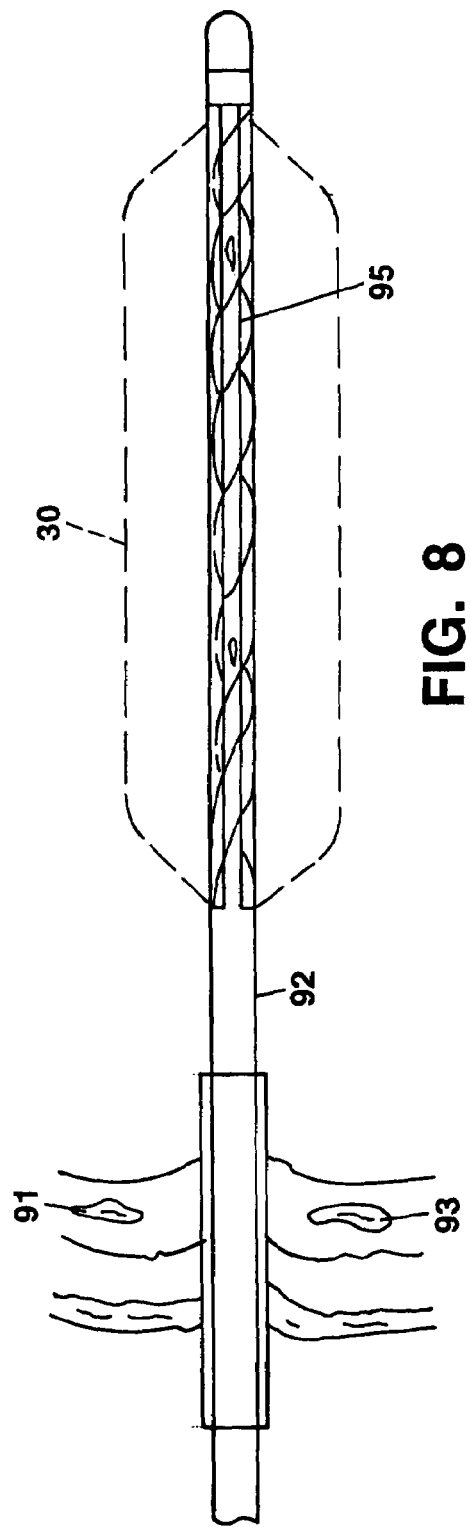

Referring to FIG. 7 and FIG. 8, there is shown a procedure illustrating one method of inserting device 30 into the body of a patient. A rigid endoscope 90 and short guide tube 94 is first inserted between the ribs 91, 93 of a patient. The endoscope 90 is then pushed toward the pancreas 34 while deflecting the patient's spleen 97. It is finally slid into position between the stomach 32 and the pancreas 34 and a desired end position 35. A second guide tube 92 (shown in FIG. 8) is then slid over the endoscope 90 to position 35. The endoscope 90 is then removed and device 30 in the form of a collapsed balloon 95 is inserted into the guide tube 92. The guide tube 92 is withdrawn and device 30 is inflated when fluid is pumped through tubular members 86, 88 shown in FIG. 4.

Figure 9:
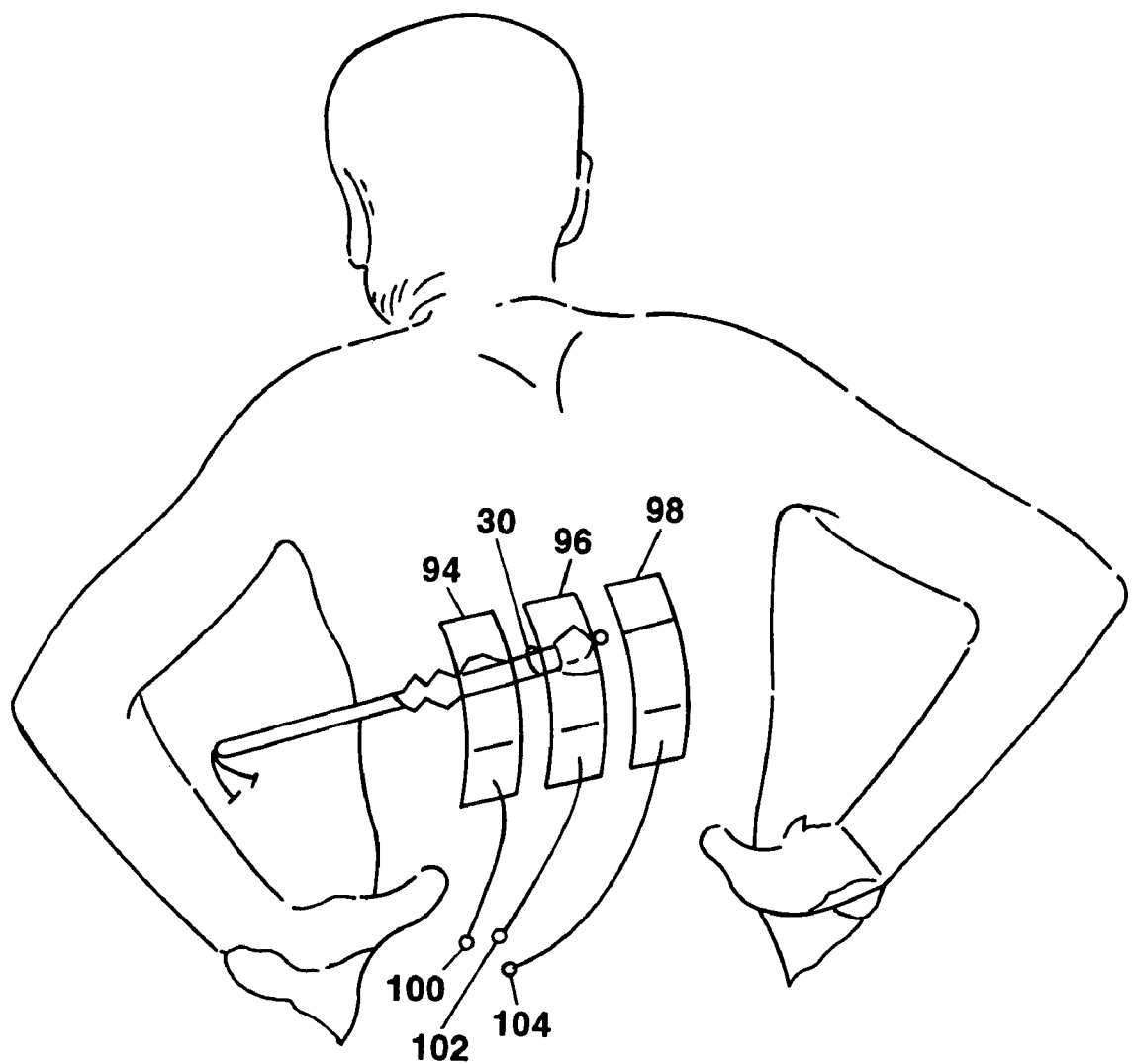
FIG. 9 shows a patient with the device shown in FIG. 4 in place and R.F. electrodes taped on the patient's back.

Referring to FIG. 9, there is shown a patient having device 30 in place and R.F. electrodes 94, 96, 98 taped to the patient's back. Each of electrodes 94, 96, 98 are electrically connected to R.F. generator 14 by wires 100, 102, 104. In operation, R.F. generator 14 (shown in FIG. 2) provides a radio frequency field between device electrodes 40, 42 (shown in FIG. 3) and electrodes 94, 96, 98 causing heating of pancreas 34 (shown in FIG. 3). In addition, as shown in FIG. 3, a surface 35 of pancreas 34 in direct contact with device 30 is alternately heated and cooled by fluid pumped through tubular members 86, 88.

Figure 10:
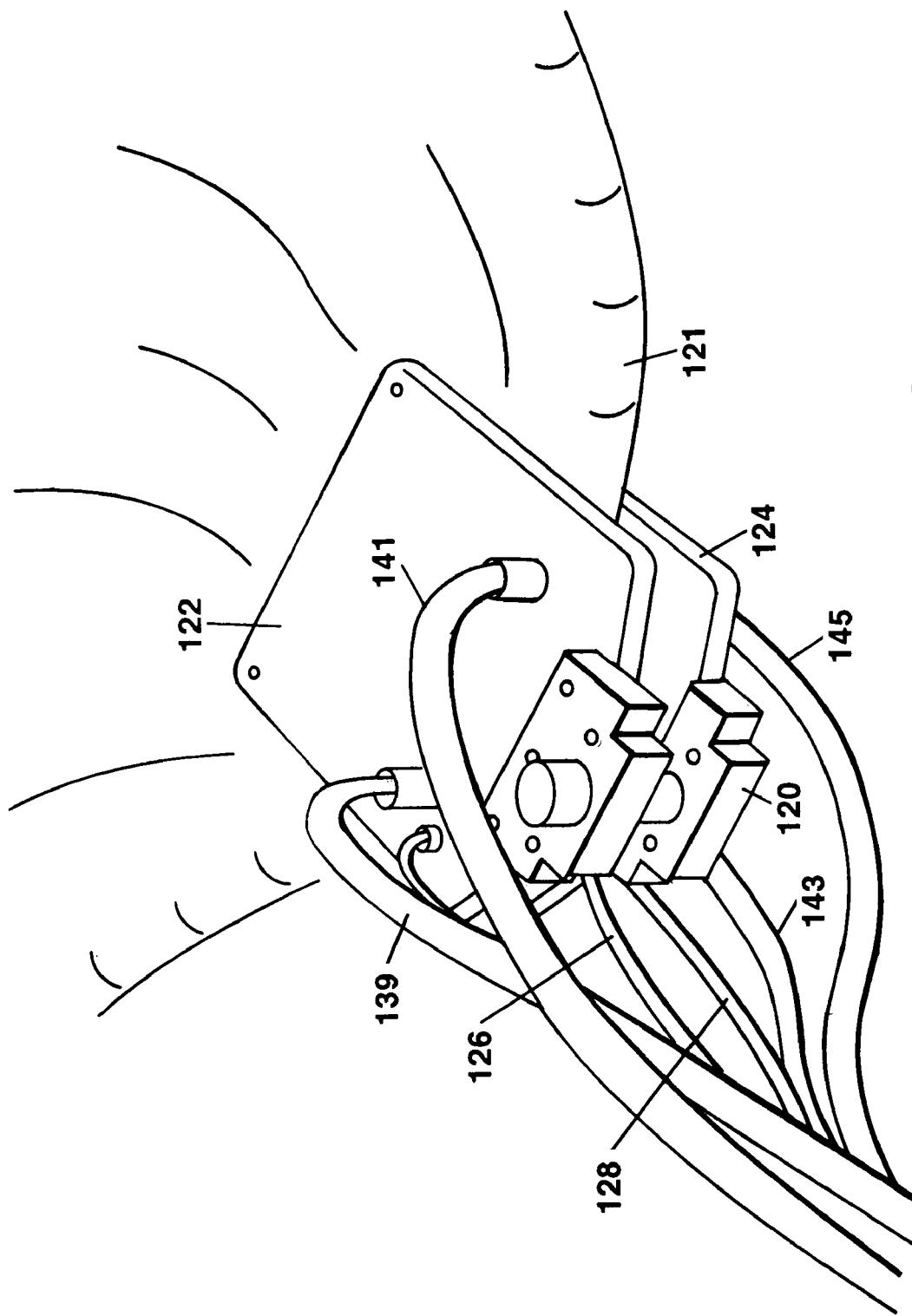
FIG. 10 shows a perspective view of a planar device suitable for treating cancer.
Figure 11:
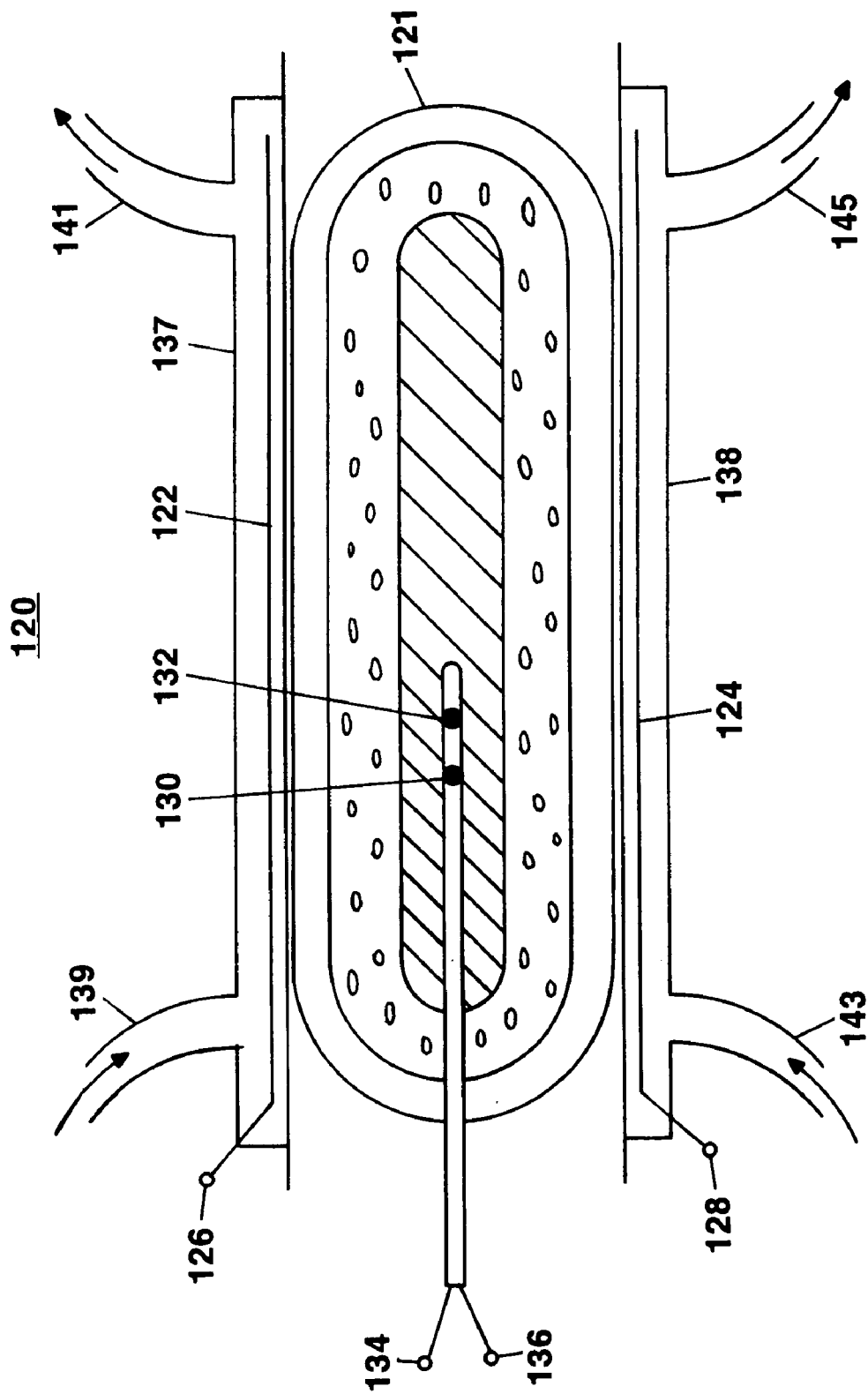
FIG. 11 shows a cross-sectional view of the device shown in FIG. 10.

Referring to FIG. 10 and FIG. 11, there is shown a perspective view and a cross-sectional view, respectively, of a planar device 120 suitable for treating cancer cells in tissue 121 between planar electrodes 122, 124. Wires 126, 128 provide an electrical connection between planar electrodes 122, 124 and R.F. generator 14 (shown in FIG. 2). Temperature sensors 130, 132 (shown in FIG. 11) are inserted into tissue 121 at different points and different depths. The temperature sensors are electrically connected by wires 134, 136 b to sensor monitor 25 (shown in FIG. 2). Water jackets 137, 138 placed against an outside surface of electrodes 122, 124 to provide heating and cooling of the surface of tissue 121 in thermal contact with electrodes 122, 124 when fluid at a desired temperature is pumped through tubular members 139, 141, 143, 145. In operation, R.F. generator 14 (shown in FIG. 2) provides an electromagnetic field between device electrodes 122, 124 causing heating of tissue 121. Planar device 120 may be suitable for treating breast cancer.

Figure 12:
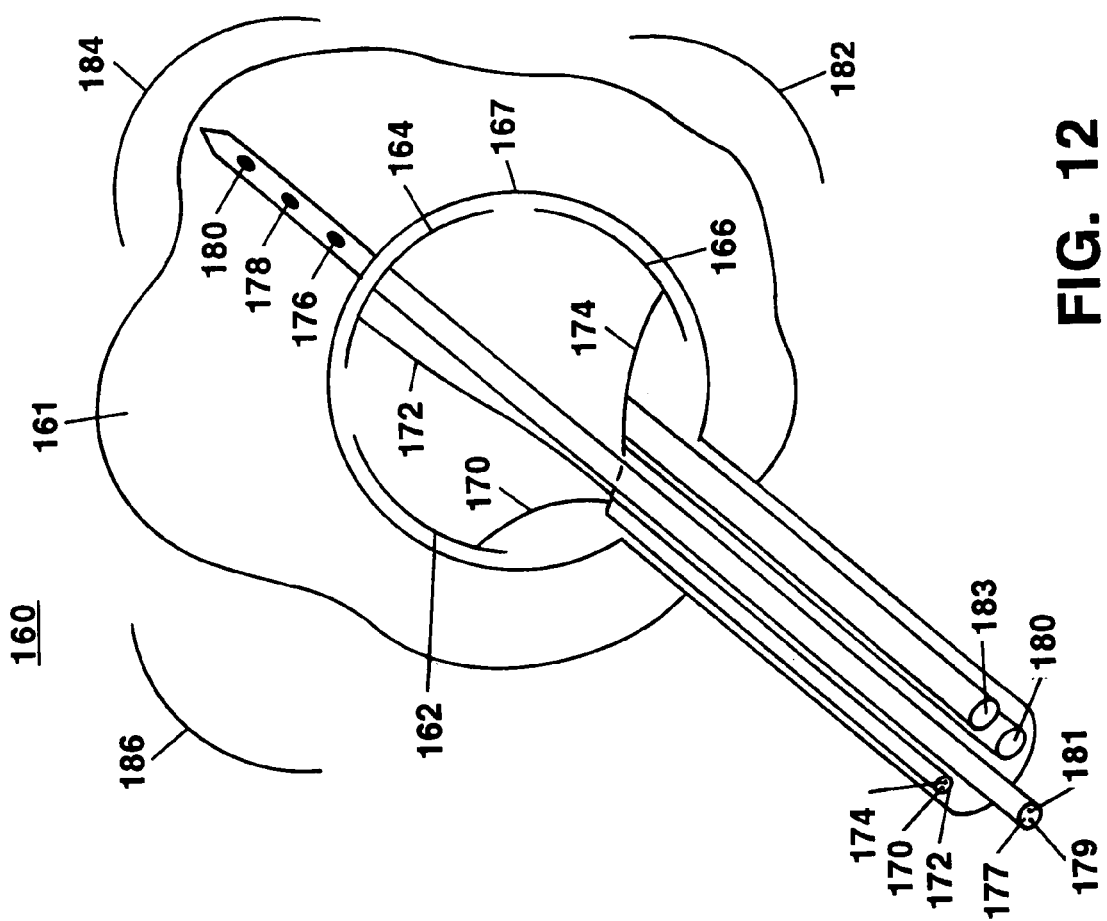
FIG. 12 shows a cross-section of a spherical device suitable for treating cancer.

Referring to FIG. 12, there is shown a cross-sectional view of a spherical device 160 suitable for treating cancer cells in tissue 161 surrounding device 160 and in contact with one or more electrodes 162, 164, 166 on an outside surface 167 of device 160. Wires 170, 172, 174 provide an electrical connection between electrodes 162, 164, 166 and R.F. generator 14 (shown in FIG. 2). Temperature sensors 176, 178, 180 are inserted into tissue 161 at different points and different depths. The temperature sensors 176, 178, 180 are electrically connected by wires 177, 179, 181 to sensor monitor 25 (shown in FIG. 2). Tubular member 180, 183 provide a path for heating and cooling fluid to the interior of device 10 for heating and cooling the surface of tissue 161 in contact with electrodes 162, 164, 166 when fluid at a desired temperature is pumped through tubular members 180, 183.

In operation, R.F. generator 14 (shown in FIG. 2) provides an electromagnetic field between device electrodes 162, 164, 166 and electrodes 182, 184, 186 also connected to R.F. generator 14 causing heating of tissue 161. Spherical device 160 may be suitable for treating prostrate cancer.

While this invention has been shown and described with reference to preferred embodiments hereof, it will be understood by those skilled in the art that various changes in form and details may be made therein without departing from the spirit and scope of the invention as defined by the appended claims.

What is claimed is:

1. A method for treating target tissue sensitive to changes in target tissue temperature comprising the steps of:

combining plurality of energy sources to generate a plurality of energy pulses;

directing said plurality of energy pulses toward said target tissue;

cooling blood flowing through said target tissue;

administering a drug for moderating the degree of blood flow cooling;

controlling said plurality of energy pulses to assist in pulsating said target tissue temperature over a predetermined period of time; and sensing and indicating temperature of said target tissue.

* * * * *